US006231559B1

(12) United States Patent
Loretti

(10) Patent No.: US 6,231,559 B1
(45) Date of Patent: May 15, 2001

(54) FLEXIBLE PLASTIC CONTAINER WITH THREE CHAMBERS

(75) Inventor: Maurice Loretti, Crissier (CH)

(73) Assignee: B. Braun Melsungen AG (DE)

( * ) Notice: Subject to any disclaimer, the term of this patent is extended or adjusted under 35 U.S.C. 154(b) by 0 days.

(21) Appl. No.: 09/289,182

(22) Filed: Apr. 9, 1999

Related U.S. Application Data

(63) Continuation-in-part of application No. PCT/EP97/05461, filed on Oct. 4, 1997.

(30) Foreign Application Priority Data

Oct. 11, 1996 (DE) ............................................. 196 41 909

(51) Int. Cl.$^{7}$ ..................................................... A61B 19/00
(52) U.S. Cl. ............................................................. 604/410
(58) Field of Search ..................................... 604/408, 410, 604/411, 415, 416, 87; 206/219, 459; 383/38, 41, 904, 906

(56) References Cited

U.S. PATENT DOCUMENTS

| | | | | |
|---|---|---|---|---|
| 4,465,488 | | 8/1984 | Richmond et al. . | |
| 4,507,114 | * | 3/1985 | Bohman et al. | 604/87 |
| 4,997,083 | | 3/1991 | Loretti et al. . | |
| 5,431,496 | * | 7/1995 | Balteau et al. | 383/38 |
| 5,560,403 | * | 10/1996 | Balteau et al. | 206/219 |
| 6,007,529 | * | 12/1999 | Gustafsson | 604/410 |
| 6,039,719 | * | 3/2000 | Wieslander et al. | 604/410 |
| 6,039,720 | * | 3/2000 | Wieslander | 604/410 |

FOREIGN PATENT DOCUMENTS

| | | |
|---|---|---|
| 3700713 | 1/1987 | (DE) . |
| 9401288 | 1/1994 | (DE) . |
| 196 05 357 | 2/1996 | (DE) . |
| 0295204 | 5/1988 | (EP) . |
| 0790051 | 2/1997 | (EP) . |
| WO9705851 | 2/1997 | (WO) . |
| WO9705852 | 2/1997 | (WO) . |

* cited by examiner

*Primary Examiner*—Dennis Ruhl
*Assistant Examiner*—Carie Mager
(74) *Attorney, Agent, or Firm*—Brobeck Phleger & Harrison, LLP

(57) ABSTRACT

The object of the invention is a flexible plastic container for the spatially separated storage and, optionally, selective sterilization of the ingredients of preparations for parenteral or enteral use. The container comprises three compartments being suited for taking up the ingredients, namely carbohydrates within compartment 3, lipids within compartment 4, and amino acids within compartment 5 as well as connections between the compartments which can be opened sterilely from the outside. The proportions by volume of the compartments are selected such that rapid mixing of all ingredients without time-consuming pressing and kneading operations by the hospital personnel is possible within compartment 5.

5 Claims, 1 Drawing Sheet

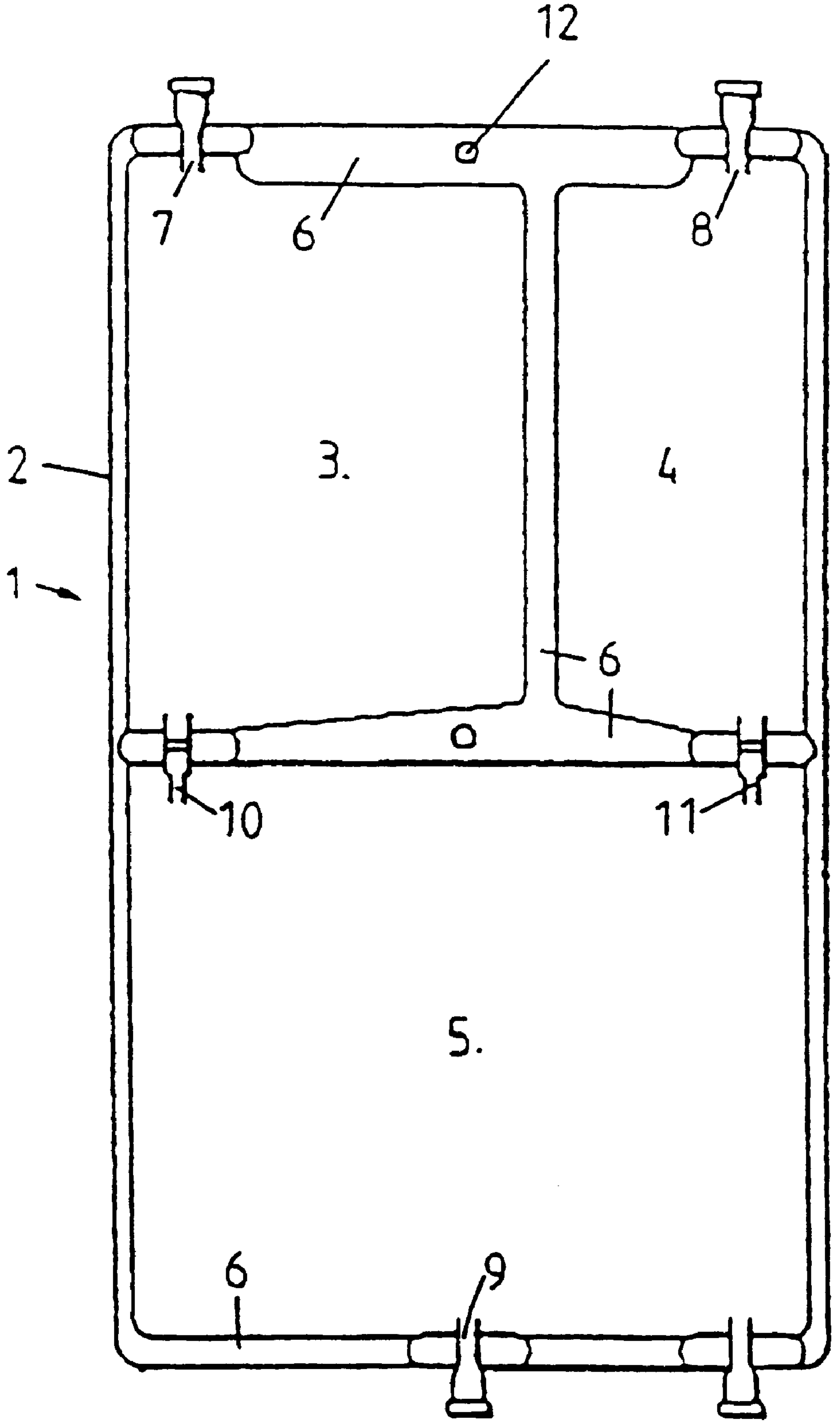
12
7
6
8
2
3.
4
1
6
10
11
5.
6
9

FLEXIBLE PLASTIC CONTAINER WITH THREE CHAMBERS

This application is a continuation-in-part of PCT Application No. PCT/EP97/05461 filed Oct. 4, 1997.

BACKGROUND OF THE INVENTION

1. Field of the Invention

The object of the invention is a flexible plastic container for the spatially separated storage and, optionally, selective sterilization of the ingredients of preparations for parenteral or enteral use comprising tree compartments and the use of the container.

2. Description of the Related Art

EP-0 295 204 B1 describes a container for medical use, in particular a container for infusions consisting of an envelope made of a flexible, homogeneous, polymerized material which is divided into three compartments separated from each other by leaktight welds of the envelope material and each of said compartments is provided with a occluded passage which can be opened deliberately to enable the contents of the part of the interior space to flow into another one, wherein the container has two adjacent parts (3,4) of the interior space within the upper portion thereof and one part (5) of the interior space within the lower portion thereof and is intended for taking up and mixing subsequently lipids, amino acids, and sugars just before the use thereof, wherein each interior part is provided with one occluded opening in order to supply the compound through said opening or to discharge the contents thereof through said opening outwards, and wherein the material of the envelope is chemically and biologically inert against any envisaged compound and the mixtures thereof.

DE 94 01 288 U1 pertains a multichamber bag having at least two chambers being arranged one upon another during the mixing stage and being surrounded by an exterior boundary, said chambers being separated from one another by at least one bar and forming an upper chamber and a mixing chamber, said bag having at least one connecting device being arranged within the bar and being closed by a locking device which is to be opened, said connecting device providing a flow connection between the chambers after being opened, said bag having at least one hang up opening at the upper boundary region and a discharge device being arranged at the mixing chamber as well as a second discharge device being opposite to said former discharge device and being arranged in the circumferential region of the mixing chamber.

With said plastic containers according to prior art mixing of the separate components of the preparations for parenteral or enteral use is possible without time-consuming kneading of the bags by the hospital personnel after opening the ports. Upon opening the ports, the ingredients of the upper compartments being in working position flow without expenditure of mechanical energy due to gravitational force into the lower mixing chamber. However, the spatial arrangement of the ingredients, in particular according to EP 0 295 204 B1, results in a relatively long mixing time before the solution can be administered to the patient.

SUMMARY OF THE INVENTION

Consequently, the problem of the present invention is to provide an improved flexible plastic container for the spatially separated storage and, optionally, selective sterilization of the ingredients of preparations for parenteral or enteral use, said container providing a more rapid and still safer mixing of all components.

The aforementioned problem of the present invention is solved by a flexible plastic container 1 for the spatially separated storage and, optionally, selective sterilization of the ingredients of preparations for parenteral or enteral use, comprising three compartments 3, 4, and 5 being separated from each other by means of leaktight welds of the envelope material, said compartments having one closable fill in opening 7, 8, and 9, each;

connecting means 10 and 11 which can be opened sterilely from the outside, by which flow connections between compartments 3, 4, and 5 can be provided; wherein the proportions by volume of compartments 3, 4, and 5 are selected such that in the working position as resulting from suspending by the hang up means 12 a rapid and complete mixture of all ingredients within compartment 5 is possible by opening the connecting means 10 and 11 and compartment 3 contains carbohydrates, compartment 4 lipids and compartment 5 amino acids.

By means of the present invention it is possible to fill in the ingredients of the preparations for parenteral or enteral use selectively into the separate compartments and to subject said ingredients to a specific, that is, in particular, stepwise sterilization. Moreover, it is therefore possible to mix ingredients adjusted to the patient with each other selectively in order to obtain homogeneous mixtures this way, if possible without additional expenditure spent by the hospital personnel.

BRIEF DESCRIPTION OF THE DRAWING

FIG. 1 is a flexible plastic container according to one embodiment of the present invention.

DETAILED DESCRIPTION OF THE INVENTION

The FIGURE represents a flexible plastic container 1 comprising three compartments 3, 4, and 5. The compartments are suited for taking up carbohydrates, fats, and amino acid solutions. In particular, the proportions by volume of the compartments are adapted such that compartment 3 is suited for taking up carbohydrates, compartment 4 is suited for taking up fats, and compartment 5 is suited for taking up amino acid solutions. The ingredients of said compartments are inserted through the closable fill in openings 7, 8, and 9, respectively, at the same time or one after another into the flexible plastic container. The ports 10 and 11 are formed as breakable valves, breakable bungs, or peelable heat sealed welds which can be opened from the outside sterilely.

Depending on the filling condition (discharged or filled) of the individual compartments, the configuration according to the invention renders it therefore possible to carry out various sterilizing processes one after another as a function of the stability of the ingredients to protect, e.g., sensitive ingredients from high temperatures or high-energy radiation. Hence, sterile ingredients can be filled into already sterile containers which have been filled already with different ingredients and treated by different sterilizing processes.

For bedside administration of the ingredient mixture, the flexible plastic container 1 according to the invention has the discharge opening being arranged at the lower circumference region of compartment 5 in the working position as resulting from suspending by the hang up means 12. This discharge opening, which may also correspond to the fill in opening 9, can optionally be provided separately beside the fill in opening 9.

In a preferred embodiment, the separate compartments are separated from each other by heat-sealed, non-peelable bars 6. These bars comprise the connecting means 10 and 11 which can be opened sterilely from the outside and by which respective flow connections between compartments 3, 4, and 5 can be provided. In addition to the connecting means 10 and 11 of the Fig. apparently corresponding and not illustrated connecting means between compartments 3 and 4 are possible, too, as said compartments are connected by common bars.

The proportions by volume of compartments 3, 4, and 5 are selected such that in the working position as resulting from suspending by hang up means 12 a complete mixing of the ingredients within the compartment 5 being arranged below them is possible by opening said connecting means 10 and 11. Rapid and complete mixing of all ingredients within compartment 5 without time-consuming pressing and kneading operations by the hospital personnel presents a particular advantage for a practical manipulation of the flexible plastic container according to the invention. Optionally, the container can comprise an additional mixing compartment being arranged below compartment 5 in the working position. This compartment is filled only when the ingredients of compartments 3, 4, and 5 are mixed.

Optionally, the flexible plastic container of the present invention has an additional hang up means in the bar region between the connecting means. This means known as such from DE 94 01 288 U1 is advantageous in that it enables reducing the volume of the relatively large, bulky plastic container being necessary for the separated storage of the ingredients for usage and administration to the patient by half. By folding down the upper half of the container comprising the discharged compartments 3 and 4 it is possible to reduce the apparent volume of the flexible plastic containers at the place of administration.

In the art several different connecting means are known which separate the contents of compartments 3, 4, and 5 from each other and permit mixing of the ingredients by opening from the outside. Therefore, providing said connecting means 10 and 11 in the form of breakable valves or breakable bungs is especially preferred within the meaning of the present invention. Alternatively, connecting means 10 and 11 can be provided in form of peelable heat-sealed welds. With the last-mentioned variant, the weld separating the ingredients of two compartments from each other is formed such that the respective flow connection is established by tearing from the outside or applying pressing pressure on the filled chambers.

An essential feature of the invention consists in the plastic container with the filled compartments 3, 4, and 5. According to the invention, filling compartment 3 with carbohydrates, compartment 4 with fats and compartment 5 with amino acids is designated. Of course, the volume of compartment 5 must be large enough to hold not only the volume of the amino acid solution in compartment 5, but also the volume of the mixture, including the volume of the contents of both compartments 3 and 4. Due to the higher density of carbohydrates in relation to amino acids, a particular simple and rapid mixing of these ingredients without time-consuming pressing and kneading operations by the hospital personnel is possible.

DE 196 05 357 A describes a flexible plastic container 1 for the spatially separated storage and, optionally, selective sterilization of the ingredients of preparations for parenteral or enteral use, comprising at least four compartments, 2, 3, 4, and 5, and, optionally, a compartment 6 being suited for taking up trace elements within compartment 2, carbohydrates within compartment 3, fats within compartment 4, and amino acid solutions within compartment 5, and, optionally, electrolytes and/or vitamins within compartment 6, said container having one of the closable fill in openings 7, 8, 9, and 10, and, optionally, 11, each;

one discharge opening 12 for administering the mixture of ingredients of the preparations for parenteral or enteral use;

connecting means 13, 13', 14, 14', and 15, 15', and, optionally, 16, 16' which can be opened sterilely from the outside, by which flow connections between the compartments 2, 3, 4, and 5, and, optionally, 6, respectively, can be provided;

wherein the proportions by volume of compartments 2, 3, 4, and 5, and, optionally, 6 are selected such that in the working position as resulting from suspending by hang up means 17 a complete mixture of all ingredients within compartment 5 is possible by opening the connecting means 13, 13', 14, 14', and 15, 15', and, optionally, 16, 16';

the proportion by volume of compartment 2 to compartment 3 is selected such that in the working position as resulting from suspending by hang up means 17 a complete mixture of the ingredients of compartments 2 and 3 within compartment 3 is possible by opening the connecting means 13, and, optionally, the proportion by volume of compartment 4 to compartment 6 is selected such that in the working position as resulting from suspending by hang up means 17 a complete mixture of the ingredients of compartments 4 and 6 within compartment 4 is possible by opening the connecting means 16, 16'.

EMBODIMENTS

Example

In a three chamber bag according to the FIGURE containing a 38.2% solution of dextrose (655 ml) in compartment 3, a customary fat emulsion (365 ml) in compartment 4, and a customary amino acid solution (640 ml) in compartment 5, a binary mixture of fat emulsion and amino acids was prepared within compartment 5. After discharging compartment 4 completely, connecting means 10 was opened and a mixture of all ingredients was obtained in compartment 5. After discharging compartment 3 completely, an infusion with a speed of 2.5 ml/min was simulated.

The quality of the mixture was observed visually.

To evaluate the mixing ratio the dextrose content was measured after varying discharge times.

The values are given in the following table 1.

TABLE 1

| Time (min) | dextrose content (g/l) nominal value 150.6 g/l |
|---|---|
| 0 | 149.0 |
| 2 | 150.6 |
| 5 | 150.0 |
| 10 | 137.3 |

TABLE 1-continued

| Time (min) | dextrose content (g/l) nominal value 150.6 g/l |
|---|---|
| 15 | 150.8 |
| 20 | 149.9 |
| 30 | 150.7 |
| 45 | 150.2 |
| 60 | 152.3 |
| 90 | 149.0 |
| 120 | 149.8 |
| 180 | 149.2 |
| 240 | 149.2 |
| 300 | 149.9 |
| 360 | 150.2 |
| 420 | 149.5 |
| 480 | 149.1 |
| 540 | 150.4 |
| 600 | 150.3 |
| 660 | 150.5 |

The table shows that without further manipulation a homogeneous mixture can be obtained if the amino acid solution is located in the lower compartment and the breakable seal 11 separating the fat emulsion from the amino acid solution is broken first.

Comparative Example

Within a three chamber bag according to the FIGURE containing the amino acid solution (640 ml) in compartment 3, the fat emulsion (365 ml) in compartment 4, and the glucose solution (655 ml) in compartment 5, a binary mixture of amino acids and glucose was prepared in compartment 5 by opening connecting means 10.

After discharging compartment 3 completely, connecting means 11 was opened and the contents of compartment 4 were introduced into compartment 5.

It turned out that no mixture of the amino acid solution and the dextrose on one hand and the fat emulsion on the other hand did occur. In any case a clear separating line between both was observed.

What is claimed is:

1. A method for preparing a material in a flexible plastic container for administration to a patient, the flexible plastic container having a first, a second and a third compartment, said first compartment formed in an upper portion of said flexible plastic container and filled with a carbohydrate solution, said second compartment formed adjacent said first compartment in said upper portion of said flexible plastic container and filled with a lipid solution, and a third compartment formed in a lower portion of said flexible plastic container and filled with an amino acid solution, said method comprising:

opening a first connecting means positioned between said second compartment and said third compartment, said opening resulting in the lipid solution in said second compartment mixing with the amino acid solution in said third compartment;

opening a second connecting means positioned between said first compartment and said third compartment, said opening resulting in the carbohydrate solution in said first compartment mixing with the amino acid solution and the lipid solution in said third compartment; and opening a valve located in said third compartment, the opening permitting the contents of the third compartment to exit the third compartment.

2. The method of claim 1, wherein gravitational force causes the lipid solution and the carbohydrate solution to flow into said third compartment when the respective connecting means is opened.

3. The method of claim 1, further comprising the step of administering the mixture of the carbohydrate solution, the lipid solution, and the amino acid solution in said third compartment to a patient.

4. The method of claim 1, wherein prior to opening said first and second connecting means, the contents of one or more of said first, second, and third compartment are selectively sterilized.

5. The method of claim 1, wherein the proportions by volume of said first, second, and third compartments are selected such that when said flexible plastic container is suspended by a hang-up means, a rapid and complete mixture of the carbohydrate solution, the lipid solution, and the amino acid solution is possible by opening said first and second connecting means.

* * * * *